(12) United States Patent
Wang et al.

(10) Patent No.: US 11,806,376 B2
(45) Date of Patent: Nov. 7, 2023

(54) PHARMACEUTICAL COMPOSITION FOR TREATING ORAL ULCER AND PREPARATION METHOD AND APPLICATION THEREOF

(71) Applicant: Sichuan Tianfu Fine Chemical Co., Ltd., Chengdu (CN)

(72) Inventors: Chongfu Wang, Chengdu (CN); Kui Wang, Chengdu (CN); Yu Gao, Chengdu (CN)

(73) Assignee: SICHUAN TIANFU FINE CHEMICAL CO., LTD., Chengdu (CN)

( * ) Notice: Subject to any disclaimer, the term of this patent is extended or adjusted under 35 U.S.C. 154(b) by 100 days.

(21) Appl. No.: 17/690,028

(22) Filed: Mar. 9, 2022

(65) Prior Publication Data
US 2023/0072566 A1    Mar. 9, 2023

(30) Foreign Application Priority Data

Sep. 2, 2021    (CN) .......................... 202111025232.9

(51) Int. Cl.
| | | |
|---|---|---|
| *A61K 36/185* | (2006.01) | |
| *A61P 17/02* | (2006.01) | |
| *A61K 31/155* | (2006.01) | |
| *A61K 35/644* | (2015.01) | |
| *A61K 36/22* | (2006.01) | |
| *A61K 36/268* | (2006.01) | |
| *A61K 36/284* | (2006.01) | |
| *A61K 36/355* | (2006.01) | |
| *A61K 36/49* | (2006.01) | |
| *A61K 36/82* | (2006.01) | |
| *A61K 36/898* | (2006.01) | |

(52) U.S. Cl.
CPC .......... *A61K 36/185* (2013.01); *A61K 31/155* (2013.01); *A61K 35/644* (2013.01); *A61K 36/22* (2013.01); *A61K 36/268* (2013.01); *A61K 36/284* (2013.01); *A61K 36/355* (2013.01); *A61K 36/49* (2013.01); *A61K 36/82* (2013.01); *A61K 36/898* (2013.01); *A61P 17/02* (2018.01)

(58) Field of Classification Search
None
See application file for complete search history.

(56) References Cited

FOREIGN PATENT DOCUMENTS

| | | | |
|---|---|---|---|
| JP | 2003201208 A | * 7/2003 | |
| TW | 200427470 A | * 12/2004 | ........... A61K 31/196 |

OTHER PUBLICATIONS

Translation attached.*

* cited by examiner

*Primary Examiner* — Terry A McKelvey
(74) *Attorney, Agent, or Firm* — WPAT, P.C

(57) ABSTRACT

A pharmaceutical composition for treating oral ulcer, a preparation method and an application thereof are provided, which belong to the technical field of pharmaceutical compositions. The pharmaceutical composition includes the following raw materials: 20-50 parts of Sanhuang mixture, 15-20 parts of lotus root powder, 30-50 parts of *Galla chinensis*, 10-20 parts of *Lonicera japonica Thunb.*, 10-20 parts of vanilla bean, 10-20 parts of propolis, 5-8 parts of oak bark, 5-10 parts of tea, 3-5 parts of *Asarum*, 1-2 parts of *Atractylodes macrocephala* and 5-30 parts of chlorhexidine acetate. The pharmaceutical composition for treating oral ulcer has the efficacies of clearing away heat, detoxifying removing blood stasis and reducing swelling, promoting granulation and relieving pain, inhibiting bacteria and killing bacteria, and has the advantages of quick response, easy finding of raw materials and low cost, and has a good therapeutic effect for treating oral ulcer clinically.

12 Claims, No Drawings

PHARMACEUTICAL COMPOSITION FOR TREATING ORAL ULCER AND PREPARATION METHOD AND APPLICATION THEREOF

TECHNICAL FIELD

The disclosure relates to the technical field of pharmaceutical compositions, and in particular to a pharmaceutical composition for treating oral ulcer, a preparation method and an application thereof.

BACKGROUND

Oral ulcer, also known as aphtha, is one of the most common diseases of oral mucosa, which refers to small and shallow defects or ulceration on oral mucosa such as tongue, cheek, lip, gum and soft palate caused by various factors. Most oral ulcers are round or oval with white or yellow center and red rim. When the oral ulcer attacks, the pain is severe, and there is a burning sensation locally, which affects eating and speaking. The prevalence rate of the general population could be as high as 20%, but the main pathogenic reasons have not yet been identified. It is believed in traditional Chinese medicine that oral ulcers are mostly caused by excessive internal heat, so clearing away heat, detoxifying, removing blood stasis and relieving pain.

It is known that the efficacy of commonly used drugs for treating oral ulcer is not very significant. Because most oral ulcers will disappear within a week or two, people generally don't pay attention to them. However, oral ulcers caused by fungi or systemic lesions will recur if not treated, and ulcers that do not heal for a long time may cause systemic lupus erythematosus and oral cancer. Therefore, it is urgent to prepare a drug for treating oral ulcer with obvious curative effect and few side effects.

SUMMARY

An objective of the disclosure is to provide a pharmaceutical composition for treating oral ulcer, a preparation method and an application thereof. The drug prescription according to the disclosure has the efficacies of clearing away heat, detoxifying removing blood stasis and reducing swelling, promoting granulation and relieving pain, inhibiting and killing bacteria, and has a good therapeutic effect for treating oral ulcer clinically.

The first technical solution of the disclosure is a pharmaceutical composition for treating oral ulcer, which includes the following components in parts by mass: 20-50 parts of Sanhuang mixture, 15-20 parts of lotus root powder, 30-50 parts of *Galla chinensis*, 10-20 parts of *Lonicera japonica Thunb.*, 10-20 parts of vanilla bean, 10-20 parts of propolis, 5-8 parts of oak bark, 5-10 parts of tea, 3-5 parts of *Asarum*, 1-2 parts of *Atractylodes macrocephala* and 5-30 parts of chlorhexidine acetate.

The Sanhuang mixture is a mixture of *Scutellaria baicalensis Georgi, Coptis chinensis Franch* and *Cortex Phellodendri*.

In an embodiment, the pharmaceutical composition includes the following components in parts by mass: 30 parts of Sanhuang mixture, 15 parts of lotus root powder, 30 parts of *Galla chinensis*, 10 parts of *Lonicera japonica Thunb.*, 20 parts of vanilla bean, 10 parts of propolis, 8 parts of oak bark, 5 parts of tea, 3 parts of *Asarum*, 2 parts of *Atractylodes macrocephala* and 15 parts of chlorhexidine acetate.

In an embodiment, a mass ratio of *Scutellaria baicalensis Georgi, Coptis chinensis Franch* and *Cortex Phellodendri* is 1:1:1.

The second technical solution of the disclosure is an application of the pharmaceutical composition for treating oral ulcer, and the pharmaceutical composition for treating oral ulcer is used for preparing drugs for treating oral ulcer.

The third technical solution of the disclosure is a pharmaceutical paste for treating oral ulcer; raw materials include the pharmaceutical composition for treating oral ulcer, calcium powder, silicon dioxide, potassium nitrate and an excipient.

In an embodiment, in parts by mass, that calcium powder is 1500-2000 parts, the silicon dioxide is 1500-2000 parts, and the potassium nitrate is 300-900 parts.

In an embodiment, the excipient includes one or more selected from a group consisting of a thickener, a humectant, a foaming agent and a flavoring agent.

In an embodiment, the thickener is one or more selected from a group consisting of guar gum, pectin, sodium alginate, cyclodextrin, sodium carboxymethyl starch, carboxymethyl cellulose, Arabic gum and SM gel;
the humectant is one or more selected from a group consisting of glycerin, sorbitol and propylene glycol;
the foaming agent is one or more selected from a group consisting of sodium dodecyl sulfate and sodium cocoyl glycine; and
the flavoring agent is one or more selected from a group consisting of turpentine oil, clove oil, mint essence and lemon grass essential oil.

Turpentine oil could promote blood circulation, reduce swelling, diminish inflammation and inhibit various bacteria. Clove oil has the efficacy of dispelling cold and relieving pain; mint essence is pungent in flavor and cool in property, and has the efficacies of dispelling wind-heat, clearing damp heat, relieving sore throat, promoting eruption, soothing liver and relieving depression. Lemon grass essential oil has antibacterial and antivirus ability, could effectively prevent contact infectious diseases, stimulate nerves, relax muscles and relieve pain.

In an embodiment, the pharmaceutical paste for treating oral ulcer could be directly applied to affected parts or tooth brushing.

The fourth technical solution of the disclosure: a preparation method of pharmaceutical paste for treating oral ulcer includes the following steps:
(1) mixing and decocting the Sanhuang mixture, the *Galla chinensis*, the *Lonicera japonica Thunb.*, the *Asarum* and the *Atractylodes macrocephala* to obtain a decoction, filtering and concentrating the decoction to obtain an extract A;
(2) extracting the vanilla bean with ethanol to obtain an extract B;
(3) crushing the oak bark, degreasing and decoloring the crushed oak bark with petroleum ether, and then performing an ethanol extraction to obtain an extract C;
(4) extracting the tea with ethanol, then extracting with chloroform and ethyl acetate sequentially, concentrating under a reduced pressure, and freeze-drying to obtain an extract D; and
(5) mixing the calcium powder, the silicon dioxide, the potassium nitrate, the extracts A, B, C and D, the lotus root powder, the propolis, the chlorhexidine acetate, a thickener and a foaming agent evenly to obtain a mixture, dispersing the obtained mixture into glycerin, and then adding with the thickener, a humectant and a flavoring agent and uniformly mixing to obtain the pharmaceutical paste for treating oral ulcer.

The pain of oral ulcer is usually caused by eating acidic substances and digestive enzymes, and calcium powder can neutralize these acidic substances and accelerate recovery. Silicon dioxide can be used as the carrier of pharmaceutical paste, with the high specific surface area, strong absorbability and active surface, silicon dioxide can adsorb the active components in drugs, so that drugs can play a greater role. Potassium nitrate can reduce the sensitivity and pain of oral ulcer.

In an embodiment, in the step (1), a relative density of the extract A at 60° is in a range of 1.15-1.25.

In an embodiment, times of the decocting in the step (1) are 2 times, and a duration of each the decocting is 2 hours. Times of the extracting the vanilla bean with ethanol in the step (2) are 3 times. In the step (3), the oak bark is crushed to 0.25-0.178 millimeters (mm), and the ethanol extraction specifically comprises: soaking the oak bark in an ethanol solution and performing microwave extraction. Times of the extracting the tea with ethanol in the step (4) are 3 times.

The disclosure has the following technical effects.

The pharmaceutical composition for treating oral ulcer according to the disclosure is mainly composed of 13 components including *Scutellaria baicalensis Georgi, Coptis chinensis Franch, Cortex Phellodendri*, lotus root powder, *Galla chinensis, Lonicera japonica Thunb.*, vanilla bean, propolis, oak bark, tea, *Asarum, Atractylodes macrocephala* and chlorhexidine acetate. Among them, *Scutellaria baicalensis Georgi* is good at clearing lung-heat, *Coptis chinensis Franch* is inclined to clear stomach heat in the middle burner and heat of heart in the upper burner, and *Cortex Phellodendri* is inclined to clear lower burner damp-heat, and the three components constitute the principle drug with the functions of clearing away heat and dampness, purging intense heat and detoxifying. Lotus root powder promotes salivation, clears away heat, invigorates spleen and reinforces the vital energy, and *Galla chinensis* detoxicates, reduces swelling, eliminates dampness and promotes wound healing, and the two are minister drugs. *Lonicera japonica Thunb.* can clear away heat and toxic materials, dispel wind-heat, vanilla bean can inhibit bacteria, propolis can resist bacteria and diminish inflammation, inhibit pathogenic bacteria, oak bark can reduce swelling and promote diuresis, clear away heat and toxic materials, and tea can scavenge free radicals and resist oxidation, and these components are adjuvant drugs. *Asarum* dissipates cold and treats exterior, *Atractylodes macrocephala* invigorates vital energy and spleen, eliminates dampness and promotes diuresis, chlorhexidine acetate inhibits bacteria and kills bacteria, and these components are used as envoy drugs. The combination of all drugs has the efficacies of clearing away heat, detoxifying removing blood stasis and swelling, promoting granulation and relieving pain, inhibiting bacteria and killing bacteria, and has a good therapeutic effect in clinical treatment of oral ulcer.

The disclosure also provides a preparation method of pharmaceutical paste for treating oral ulcer, the pharmaceutical paste is composed of 13 components including *Scutellaria baicalensis Georgi, Coptis chinensis Franch, Cortex Phellodendri*, lotus root powder, *Galla chinensis, Lonicera japonica Thunb.*, vanilla bean, propolis, oak bark, tea, *Asarum, Atractylodes macrocephala* and chlorhexidine acetate; the extraction process of medicinal materials is different for different effective components of different drug components. Ferulic acid as the effective component in vanilla bean is fat-soluble, so ethanol extraction is adopted. Quercetin in oak bark has a good extraction effect after crushing, decoloration and ethanol microwave treatment. Tea polyphenols in tea are extracted with ethanol, and then extracted with chloroform and ethyl acetate to obtain tea polyphenols with higher purity. Other medicinal materials are extracted with water to extract effective substances, and finally combined to make preparations, the method can ensure that the effective components can be retained to the greatest extent in the preparation process and improve the therapeutic efficacy of the pharmaceutical paste. The pharmaceutical excipient is composed of calcium powder, silicon dioxide, potassium nitrate, thickener, humectant, foaming agent and flavoring agent, and the excipient is prepared after these materials are uniformly dispersed and the product is easy to use.

The *Galla chinensis* extract according to the disclosure contains tannic acid, which can coagulate the protein of local tissues such as skin, mucosa, ulcer, etc. to converge and accelerate blood coagulation to stop bleeding. Tea polyphenols in tea extract can protect the vitamins in lotus root powder from oxidation, and can improve the ability of vitamins to promote the healing of ulcer surface, and the combination of vitamins and tea polyphenols has a good therapeutic effect. Ferulic acid in the extract of vanilla bean has good antibacterial and anti-inflammatory effects. Quercetin in oak bark extract can temporarily inhibit saliva secretion in the oral cavity, so that the drug can better adhere to the diseased part and exert its efficacy. Chlorhexidine acetate is an externally applied disinfection products with high efficiency and no toxic and side effects; it is commonly used in mouthwash, etc., and can kill a variety of common oral bacteria and play a supporting role in healing oral ulcer. The disclosure also adds propolis, which can improve immunity, resist bacteria and diminish inflammation, inhibit the growth and reproduction of pathogenic bacteria, and has pretty good efficacy of inhibiting and killing viruses.

DETAILED DESCRIPTION OF EMBODIMENTS

Various exemplary embodiments of the disclosure will be described in detail below. This detailed description should not be considered as a limitation of the disclosure, but should be understood as a more detailed description of some aspects, characteristics and embodiments of the disclosure.

It should be understood that the terms used in this disclosure are only for describing specific embodiments, and are not used to limit the disclosure. In addition, for the numerical range in the disclosure, it should be understood that each intermediate value between the upper limit and the lower limit of the range is also specifically disclosed. Any stated value or intermediate value within the stated range and any other stated value or every smaller range between intermediate values within the stated range are also included in the disclosure. The upper and lower limits of these smaller ranges could be independently included or excluded from the range.

Unless otherwise specified, all technical and scientific terms used herein have the same meaning as commonly understood by the ordinary technicians in the field of this disclosure. Although the disclosure only describes the preferred methods and materials, any methods and materials similar or equivalent to those described herein can also be used in the practice or testing of the disclosure. All documents mentioned in this description are incorporated by reference to disclose and describe the methods and/or materials related to the documents. In case of conflict with any incorporated documents, the contents of this specification shall prevail.

Without departing from the scope or spirit of the disclosure, it is obvious to those skilled in the art that many modifications and changes could be made to the specific embodiments of the disclosure. Other embodiments obtained from the description of the disclosure will be obvious to those skilled. The description and embodiments of this disclosure are exemplary only.

The words "including", "comprising", "having" and "containing" used in this paper are all open terms, that is, they mean including but not limited to.

Embodiment 1

(1) Weighing raw materials according to Table 1.

TABLE 1

| Scutellaria baicalensis Georgi | 100 grams (g) | Propolis | 100 g |
|---|---|---|---|
| Coptis chinensis Franch | 100 g | Oak bark | 80 g |
| Cortex Phellodendri | 100 g | Tea | 50 g |
| Lotus root powder | 150 g | Asarum | 30 g |
| Galla chinensis | 300 g | Atractylodes macrocephala | 20 g |
| Vanilla bean | 200 g | Chlorhexidine acetate | 150 g |
| Lonicera japonica Thunb. | 100 g | | |

Excipient: 18000 g of calcium powder, 18000 g of silicon dioxide, 6000 g of potassium nitrate, 600 g of carboxymethyl cellulose, 12000 g of glycerin, 1800 g of sodium dodecyl sulfate, 600 g of SM gel, 6000 g of sorbitol and 600 g of mint essence.

(2) Mixing and decocting Sanhuang mixture including *Scutellaria baicalensis Georgi*, *Coptis chinensis Franch* and *Cortex Phellodendri*, *Galla chinensis*, *Lonicera japonica Thunb.*, *Asarum* and *Atractylodes macrocephala* to obtain a mixture and then decocting the mixture with water for two times, including: decocting the mixture for 2 hours with 6 times of water in the first time to thereby obtain a first decoction, and separating the first decoction to obtain a first filtrate and a first filter residue; decocting the first filter residue for 2 hours with 4 times of water in the second time to thereby obtain a second decoction, and separating the second decoction to obtain a second filtrate; combining the first filtrate and the second filtrate, filtering the combined filtrate to obtain a third filtrate, and concentrating the third filtrate to a thick paste with a relative density in a range of 1.15-1.25 grams per milliliter (g/mL) (60° C.) to obtain an extract A.

(3) Refluxing and extracting vanilla bean with 70% ethanol (volume fraction) for three times, including: adding 4 times volume of 70% ethanol for the first time, and adding 2 times volume of 70% ethanol for the second time and the third time respectively; combining the extracts after three times of reflux extraction, and concentrating and drying the combined extracts to obtain an extract B.

(4) Crushing oak bark to 0.25 mm, adding 2 times volume of petroleum ether for degreasing and decoloring the crushed oak bark with petroleum ether, removing petroleum ether, and then adding 4 times volume of 50% ethanol (volume fraction), extracting the crushed oak bark with 50% ethanol with 200 watts (W) microwave for 30 minutes to thereby obtain a crude extract, concentrating the crude extract under reduced pressure, and vacuum drying the concentrated crude extract to obtain an extract C.

(5) Leaching tea with 60% ethanol (volume fraction) for three times, including: adding 4 times volume of 60% ethanol for the first leaching and leaching tea in a water bath at 80° C. for 0.5 hours to thereby obtain a first leaching solution, adding 2 times volume of 60% ethanol in the tea after the first leaching for the second leaching and leaching tea in a water bath at 80° C. for 0.5 hours to thereby obtain a second leaching solution, and adding 2 times volume of 60% ethanol in the tea after the second leaching for the third leaching and leaching tea in a water bath at 80° C. for 0.5 hours to thereby obtain a third leaching solution; combining the three leaching solutions, extracting the combined leaching solutions twice with chloroform and ethyl acetate sequentially to thereby obtain a crude extract of the tea, concentrating the crude extract of the tea under reduced pressure, and freeze-drying the concentrated crude extract of the tea at −20° C. to obtain an extract D.

(6) mixing calcium powder, silicon dioxide, potassium nitrate, extracts A-D, lotus root powder, propolis, chlorhexidine acetate, carboxymethyl cellulose and sodium dodecyl sulfate uniformly to obtain a target mixture, dispersing the target mixture into glycerin, and then adding SM gel, sorbitol and mint essence and uniformly mixing the dispersed mixture to obtain the pharmaceutical paste for treating oral ulcer.

Embodiment 2

Embodiment 2 is carried out in the same way as the embodiment 1 except that the raw materials are weighed according to Table 2.

TABLE 2

| Scutellaria baicalensis Georgi | 66.7 g | Propolis | 100 g |
|---|---|---|---|
| Coptis chinensis Franch | 66.7 g | Oak bark | 50 g |
| Cortex Phellodendri | 66.7 g | Tea | 50 g |
| Lotus root powder | 150 g | Asarum | 30 g |
| Galla chinensis | 300 g | Atractylodes macrocephala | 10 g |
| Vanilla bean | 100 g | Chlorhexidine acetate | 50 g |
| Lonicera japonica Thunb. | 100 g | | |

Embodiment 3

Embodiment 2 is carried out in the same way as the embodiment 1 except that the raw materials are weighed according to Table 3.

TABLE 3

| | | | |
|---|---|---|---|
| Scutellaria baicalensis Georgi | 166.7 g | Propolis | 200 g |
| Coptis chinensis Franch | 166.7 g | Oak bark | 80 g |
| Cortex Phellodendri | 166.7 g | Tea | 100 g |
| Lotus root powder | 200 g | Asarum | 50 g |
| Galla chinensis | 500 g | Atractylodes macrocephala | 20 g |
| Vanilla bean | 200 g | Chlorhexidine acetate | 300 g |
| Lonicera japonica Thunb. | 200 g | | |

Comparative Example 1

Comparative example 1 is carried out in the same way as the embodiment 1 except that *Galla chinensis* is omitted, and the dosages of *Scutellaria baicalensis Georgi*, *Coptis chinensis Franch* and *Cortex Phellodendri* are all 200 g.

Comparative Example 2

Comparative example 2 is carried out in the same way as the embodiment 1 except that *Coptis chinensis Franch* is omitted, and the dosage of *Cortex Phellodendri* is 200 g.

Comparative Example 3

Comparative example 3 is carried out in the same way as the embodiment 1 except that vanilla bean is omitted, and the dosage of *Galla chinensis* is 500 g.

Comparative Example 4

Comparative example 4 is carried out in the same way as the embodiment 1 except that tea is omitted and the dosage of *Asarum* is 80 g.

Comparative Example 5

Comparative example 1 is carried out in the same way as the embodiment 1 except that oak bark is omitted, the dosage of propolis is 140 g, and the dosage of tea is 90 g.

Comparative Example 6

Comparative example 6 is carried out in the same way as the embodiment 1 except that 600 g of mint essence is omitted, and the dosage of sorbitol is 6600 g.

Comparative Example 7

Comparative example 7 is carried out in the same way as the embodiment 1 except that the microwave ultrasonic extraction in the step (4) is replaced by water bath extraction at 60° C.

Effect Example 1

The pharmaceutical pastes for treating oral ulcer prepared in the Embodiment 1 and the comparative examples 1-7 are used to test the healing of experimental oral ulcer. The experimental design, process implementation and experimental results are as follows:

(1) 120 mice are randomly grouped into model control group, Littino-compound benzocaine gel group (positive control group), the embodiments 1-3 of the disclosure and the comparative examples 1-7, totally 12 groups, 10 mice in each group. Mice in each group are anesthetized with ether and fixed on the mouse plates on their back. Taking a glass tube with a diameter of 3 mm; placing a small cotton ball at one end of the tube to make the cotton ball flush with the mouth of tube; immersing the cotton ball end of the glass tube in a phenol solution with a mass fraction of 850 grams per liter (g/L) to make the liquid medicine soak the cotton ball; placing the cotton ball on the buccal mucosa of mouse and burning for about 60 seconds. After removing the glass tube, it can be seen that there is a white lesion with a diameter of 3-4 mm in this area; the next day, it can be seen that the rat's lips are moist, drooling, and the buccal mucosa is red and swollen, that is, the modeling of oral ulcer is successful.

(2) Compound benzocaine gel group: applying 2 micrograms per gram (mg/g) of compound benzocaine gel, with an average of 5 times at intervals of 4 hours; the embodiments 1-3 and the comparative examples 1-7: applying 2 mg/g of the pharmaceutical paste prepared in the embodiments 1-3 of the disclosure and the comparative examples 1-7 respectively, with an average of 5 times at intervals of 4 hours; no administration for the model control group.

For the above-mentioned compound benzocaine gel group, the embodiments 1-3 of the disclosure and the comparative examples 1-7, carrying out fasting and water deprivation for 30 minutes after each administration; after continuous administration for 6 days, observing the healing of oral ulcer in mice, and recording the diameter (in mm) of oral ulcer surface and the healing number of oral ulcer in mice. Healing standard: ulcer diameter <1 mm represents healing, and ulcer diameter ≥1 mm represents unhealing. The results are shown in Table 4.

TABLE 4

Comparison of oral ulcer surface diameters of mice in each group

| Group | Total number of animals (piece) | Number of healed animals after 6 days of administration (piece) | Healing rate (%) |
|---|---|---|---|
| Model control group | 10 | 1 | 10 |
| Positive control group | 10 | 9 | 90 |
| Embodiment 1 group | 10 | 10 | 100 |
| Embodiment 2 group | 10 | 10 | 100 |
| Embodiment 3 group | 10 | 10 | 100 |
| Comparative example 1 group | 10 | 7 | 70 |
| Comparative example 2 group | 10 | 8 | 80 |
| Comparative example 3 group | 10 | 7 | 70 |
| Comparative example 4 group | 10 | 9 | 90 |
| Comparative example 5 group | 10 | 9 | 90 |

TABLE 4-continued

Comparison of oral ulcer surface diameters of mice in each group

| Group | Total number of animals (piece) | Number of healed animals after 6 days of administration (piece) | Healing rate (%) |
|---|---|---|---|
| Comparative example 6 group | 10 | 9 | 90 |
| Comparative example 7 group | 10 | 9 | 90 |

Healing rate = (number of healed animals/total number of animals) × 100%.

As can be seen from the Table 4, the pharmaceutical paste prepared in the Embodiment 1 of the disclosure has a good curative effect on oral ulcer in mice, and can significantly improve the cure rate.

Effect Example 2

From 2015 to 2020, 100 patients with ulcer were treated and grouped into two groups according to the random number table method, treatment group 1 and treatment group 2. There was no significant difference in the basic information, age and course of disease among 100 patients.

Patients in the treatment group were treated as follows: the pharmaceutical paste described in the embodiment 1 was taken and applied to the wound of oral ulcer twice a day, 0.5 hours before breakfast and 1 hour after dinner, and one week was a course of treatment; and all patients were treated for one course of treatment, follow-up observation and recording were kept during the treatment.

Patients in the second treatment group were treated as follows: compound benzocaine gel was taken and applied to the wound of oral ulcer twice a day, 0.5 hours before breakfast and 1 hour after dinner, and one week was a course of treatment; and all patients were treated for one course of treatment, follow-up observation and recording were kept during the treatment.

Criterion of curative effect: recovered: all clinical symptoms disappeared; strikingly effective: ulcer wound healed and pain disappeared; effective: the ulcer area is reduced by ≥½, and the pain is not obvious; ineffective: the symptoms have not improved or the ulcer area has shrunk by <⅓, and the patient still can't eat comfortably.

TABLE 5

Therapeutic effects

| Group | Number of cases | Recovered | Strikingly effective | Effective | Ineffective | Total effective rate (%) |
|---|---|---|---|---|---|---|
| Treatment group 1 | 100 | 75 | 15 | 5 | 5 | 95 |
| Treatment group 2 | 100 | 65 | 13 | 4 | 18 | 82 |

Total effective rate = (recovered + strikingly effective + effective)/number of cases × 100%.

The above-mentioned embodiments only describe the preferred mode of the disclosure, and do not limit the scope of the disclosure. Without departing from the design spirit of the disclosure, all kinds of modifications and improvements made by ordinary technicians in the field to the technical scheme of the disclosure should fall within the protection scope determined by the claims of the disclosure.

What is claimed is:

1. A pharmaceutical composition for treating oral ulcer, comprising the following components in parts by weight:
   30 parts of Sanhuang mixture,
   15 parts of lotus root powder,
   30 parts of *Galla chinensis*,
   10 parts of *Lonicera japonica* Thunb.,
   20 parts of vanilla bean,
   10 parts of propolis,
   8 parts of oak bark,
   5 parts of tea,
   3 parts of *Asarum*,
   2 parts of *Atractylodes macrocephala*, and
   15 parts of chlorhexidine acetate;
   wherein the Sanhuang mixture is a mixture of *Scutellaria baicalensis* Georgi, *Coptis chinensis* Franch and *Cortex Phellodendri*;
   wherein the pharmaceutical composition is prepared into a pharmaceutical paste.

2. The pharmaceutical composition for treating oral ulcer according to claim 1, wherein a weight ratio of *Scutellaria baicalensis* Georgi, *Coptis chinensis* Franch and *Cortex Phellodendri* is 1:1:1.

3. The pharmaceutical composition according to claim 1, wherein the pharmaceutical composition for treating oral ulcer is applied in preparing a drug for treating oral ulcer.

4. The pharmaceutical composition according to claim 2, wherein the pharmaceutical composition for treating oral ulcer is applied in preparing a drug for treating oral ulcer.

5. A pharmaceutical paste for treating oral ulcer, wherein raw materials of the pharmaceutical paste comprise the pharmaceutical composition for treating oral ulcer according to claim 1, calcium powder, silicon dioxide, potassium nitrate and an excipient.

6. The pharmaceutical paste according to claim 5, wherein in parts by weight, the calcium powder is 1500-2000 parts, the silicon dioxide is 1500-2000 parts and the potassium nitrate is 300-900 parts.

7. The pharmaceutical paste according to claim 5, wherein the excipient comprises one or more selected from a group consisting of a thickener, a humectant, a foaming agent and a flavoring agent.

8. A preparation method of the pharmaceutical paste for treating oral ulcer according to claim 5, comprising:
   step (1), mixing and decocting the Sanhuang mixture, the *Galla chinensis*, the *Lonicera japonica* Thunb., the *Asarum* and the *Atractylodes macrocephala* to obtain a decoction, filtering and concentrating the decoction to obtain an extract A;
   step (2), extracting the vanilla bean with ethanol to obtain an extract B;
   step (3), crushing the oak bark, degreasing and decoloring the crushed oak bark with petroleum ether, and then performing an ethanol extraction to obtain an extract C;
   step (4), extracting the tea with ethanol, then extracting with chloroform and ethyl acetate sequentially, concentrating under a reduced pressure, and freeze-drying to obtain an extract D; and
   step (5), mixing the calcium powder, the silicon dioxide, the potassium nitrate, the extracts A, B, C and D, the lotus root powder, the propolis, the chlorhexidine acetate, a thickener and a foaming agent uniformly to obtain a mixture, dispersing the obtained mixture into glycerin, and then adding with the thickener, a humectant and a flavoring agent and uniformly mixing to obtain the pharmaceutical paste for treating oral ulcer.

9. The preparation method according to claim 8, wherein in the step (1), a relative density of the extract A at 60° C. is in a range of 1.15-1.25.

10. The preparation method according to claim 8, wherein times of the decocting in the step (1) are 2 times, and a duration of each the decocting is 2 hours;
   wherein times of the extracting the vanilla bean with ethanol in the step (2) are 3 times;
   wherein in the step (3), the oak bark is crushed to 0.25-0.178 millimeters (mm), and the ethanol extraction specifically comprises: soaking the oak bark in an ethanol solution and performing microwave extraction; and
   wherein times of the extracting the tea with ethanol in the step (4) are 3 times.

11. The preparation method according to claim 8, wherein in parts by weight, the calcium powder is 1500-2000 parts, the silicon dioxide is 1500-2000 parts and the potassium nitrate is 300-900 parts.

12. The preparation method according to claim 8, wherein the excipient comprises the thickener, the humectant, the foaming agent and the flavoring agent.

* * * * *